United States Patent
Zheng et al.

(10) Patent No.: US 10,821,307 B2
(45) Date of Patent: Nov. 3, 2020

(54) HONEYCOMB RIB STRUCTURE IN ROTATING GANTRY OF PROTON THERAPY DEVICE

(71) Applicant: HEFEI CAS ION MEDICAL AND TECHNICAL DEVICES CO., LTD., Hefei, Anhui (CN)

(72) Inventors: Jinxing Zheng, Anhui (CN); Ming Li, Anhui (CN); Yuntao Song, Anhui (CN); Wuquan Zhang, Anhui (CN); Yong Cheng, Anhui (CN); Songzhu Yang, Anhui (CN); Yu Zhang, Anhui (CN)

(73) Assignee: HEFEI CAS ION MEDICAL AND TECHNICAL DEVICES CO., LTD., Heifei (CN)

( * ) Notice: Subject to any disclaimer, the term of this patent is extended or adjusted under 35 U.S.C. 154(b) by 49 days.

(21) Appl. No.: 16/207,204

(22) Filed: Dec. 3, 2018

(65) Prior Publication Data
US 2019/0111285 A1 Apr. 18, 2019

Related U.S. Application Data

(63) Continuation of application No. PCT/CN2017/115353, filed on Dec. 9, 2017.

(30) Foreign Application Priority Data

Dec. 13, 2016 (CN) .......................... 2016 1 1142807

(51) Int. Cl.
*A61N 5/10* (2006.01)

(52) U.S. Cl.
CPC .... *A61N 5/1081* (2013.01); *A61N 2005/1087* (2013.01)

(58) Field of Classification Search
CPC ....................................................... A61N 5/10
See application file for complete search history.

(56) References Cited

U.S. PATENT DOCUMENTS

| | | | | |
|---|---|---|---|---|
| 8,822,931 B2* | 9/2014 | Laurence | ................ | G01T 1/164 250/362 |
| 2006/0013354 A1* | 1/2006 | Heismann | .............. | A61B 6/032 378/4 |
| 2006/0013355 A1* | 1/2006 | Heismann | .............. | A61B 6/032 378/4 |
| 2010/0027759 A1 | 2/2010 | Luecke | | |

(Continued)

FOREIGN PATENT DOCUMENTS

| CN | 1681436 A | 10/2005 |
|---|---|---|
| CN | 1778274 A | 5/2006 |

(Continued)

*Primary Examiner* — Thomas R Artman

(57) ABSTRACT

A honeycomb rib structure in a rotating gantry of a proton includes an upper honeycombed rib plate and a lower honeycombed rib plate which are mounted in a cylindrical body through a plurality of connecting structures. The upper and lower honeycombed rib plates are symmetrically arranged, and are spliced by a plurality of basic structures which are in a regular hexagonal shape. Connecting nodes between the adjacent basic structures are of a ring structure. Densities of the upper and lower honeycombed rib plates are adjusted through a density increasing structure.

6 Claims, 3 Drawing Sheets

(56) References Cited

U.S. PATENT DOCUMENTS

2012/0228522 A1    9/2012  Sasai
2013/0256537 A1*  10/2013  Laurence ................. G02B 6/10
                                                              250/362
2019/0111285 A1*  4/2019  Zheng ................. A61N 5/1081

FOREIGN PATENT DOCUMENTS

| CN | 1923141 A   | 3/2007  |
|----|-------------|---------|
| CN | 101244317 A | 8/2008  |
| CN | 104735891 A | 6/2015  |
| CN | 104825181 A | 8/2015  |
| CN | 104837526 A | 8/2015  |
| CN | 105797281 A | 7/2016  |
| CN | 106051058 A | 10/2016 |
| CN | 106492357 A | 3/2017  |
| CN | 206715057 U | 12/2017 |

* cited by examiner

HONEYCOMB RIB STRUCTURE IN ROTATING GANTRY OF PROTON THERAPY DEVICE

CROSS-REFERENCE TO RELATED APPLICATIONS

This application is a continuation of International Application No. PCT/CN2017/115353, filed on Dec. 9, 2017, which claims priority from Chinese Patent Application No. 201611142807.4, filed on Dec. 13, 2016, both of which are hereby incorporated by reference in their entireties.

TECHNICAL FIELD

The present disclosure relates to medical devices, and more particularly to a honeycomb rib structure for installing a rotating gantry of a proton therapy device.

BACKGROUND

Cancer (malignant tumors) has become one of the leading causes of death among people in the world. New technologies for the cancer treatment in various countries are emerging. Radiotherapy in the traditional cancer treatment mainly adopts X-ray, γ-ray and electron beam, and its physical dose distribution and biological effect damage the normal cells near the tumor to varying degrees. And the effective utilization rate of the dose is also low. Although biological effects of the neutron and the negative π particle are good, their physical dose distributions excessively damage the normal tissues. Therefore, the radiotherapy is not the ideal treatment method. The advantage of the proton therapy is that the radiation energy peak is targeted at the tumor lesion so that the radiation dose applied to the tumor lesion is maximized. Normal cells closer to the therapy device than the tumor are usually only subjected to ⅓-½ of the peak dose, and the normal cells away from the therapy device and blocked by the tumor cells are substantially undamaged. The proton therapy is much superior to the conventional radiotherapy thanks to the inherent physical property of the proton. In recent decades, more than 100,000 cancer patients have been treated by the proton therapy. Thus, the superiority of the proton therapy has been widely clinically proven.

Currently, the proton therapy centers that have been successfully operated have the disadvantages of large size, high cost, long construction period and difficulty in popularization, and the proton therapy device used in these proton therapy centers does not have the function of locating the cancer cells, so that additional device is required for determining the location of the cancer cells by diagnosing the patient before treating the patient with the proton therapy device. The mainstream development direction of the proton therapy device in the future is miniaturization and integration, which reduces the overall size of the proton therapy device, shortens the construction period, reduces the cost, and integrates the diagnostic test with the treatment to facilitate the popularization of the proton therapy device.

The honeycomb structure is the basic structure of the honeycomb. It is a structure composed of a plurality of regular hexagonal cells in a back-to-back symmetrical arrangement with all openings of the cells facing downwardly or facing toward a side. This structure has an excellent geometric mechanical structure and a wide range of applications in many subjects. The spacecraft adopted with the honeycomb structure has high strength and light weight. Therefore, the honeycomb structure is very suitable for installing in the rotating gantry of the proton therapy device, and realizes the lightweight of the rotating gantry under the premise of satisfying the structural strength.

In addition, in the ninth issue of the fourth volume of *Nuclear Technology*, titled "Magnetic Field Measurement on the Electron-Ring Magnets of HERA Proton-Electron Collider", a device for measuring the magnetic field intensity by means of screw-driven translation coil is disclosed. The problem is that the device has low measurement accuracy with a large space occupied by the system. Therefore, the device is not suitable for measuring the magnetic field of the compact cyclotron.

SUMMARY

The objective of the present disclosure is to provide a honeycomb rib structure suitable for installing in a rotating gantry of a proton therapy device, which can meet the requirement on the lightweight of the rotating gantry of the proton therapy device, realize the structural strength of the rotating gantry to meet the design requirements, and greatly reduce the manufacturing cost. At the same time, the density of the rib structure can be adjusted through the special design, and the structural strength of the rib structure can be improved to meet the structural requirements under different conditions.

A honeycomb rib structure in a rotating gantry of a proton therapy device includes an upper honeycombed rib plate and a lower honeycombed rib plate, which are mounted in a cylindrical body through a plurality of connecting structures. The upper honeycombed rib plate and the lower honeycombed rib plate are symmetrically arranged, and are spliced by a plurality of basic structures, wherein each of the basic structures is in a regular hexagonal shape. Connecting nodes between the adjacent basic structures are ring structures. Densities of the upper honeycombed rib plate and the lower honeycombed rib plate are adjusted through a density increasing structure.

The cylindrical body is the rotating gantry of the proton therapy device, and the upper honeycombed rib plate and the lower honeycombed rib plate are mounted in the cylindrical body.

The ring structure is in a columnar shape. Through holes are provided in the ring structures in a radial direction, and the upper honeycombed rib plate and the lower honeycombed rib plate are connected through bolts.

The upper honeycombed rib plate and the lower honeycombed rib plate are connected to the cylindrical body through the plurality of connecting structures. Each of the plurality of connecting structures has four casing walls in which every two casing walls with the same shape are oppositely arranged, respectively. Bottoms of the plurality of connecting structures are fitted to an inner annular wall of the cylindrical body. An upper side of each of the plurality of connecting structures is open. Six pairs of the connecting structures are uniformly arranged on the inner annular wall of the cylindrical body, and a plurality of clamping grooves are provided in middle portions of two pairs of the connecting structures which are correspondingly arranged.

The plurality of connecting structures are clamped by ring side openings of the upper honeycombed rib plate and the lower honeycombed rib plate, and straight plates of the upper honeycombed rib plate and the lower honeycombed rib plate are clamped in the plurality of clamping grooves in the middle portions of the corresponding connecting structures.

The density increasing structure which is in a U shape is connected to the upper honeycombed rib plate and the lower honeycombed rib plate through the ring structures. The density increasing structure includes a connecting plate and two round rods. Both end faces of the connecting plate are perpendicularly connected to the two round rods, respectively. The connecting plate is flush with connecting ends of the two round rods. An outer diameter of each of the two round rods is matched with an inner diameter of the ring structures, and the two round rods are inserted into the through holes of the ring structures.

The present disclosure has the following beneficial effects:

The internal structure of the cylindrical body of the rotating gantry of the proton therapy device can be strengthened. The weight of the rotating gantry can be fully reduced under the premise of satisfying the structural strength of the cylindrical body, thereby reducing the manufacturing cost of the rotating gantry. The structural process of the honeycomb rib plates is simple. The density of the honeycomb rib plates can be adjusted according to actual needs, which reduces the processing cost. The present disclosure has important significance for promoting the proton therapy technology.

BRIEF DESCRIPTION OF THE DRAWINGS

To make those skilled in the art understand better, the present disclosure will be further described below with reference to the accompanying drawings.

Figure 1:
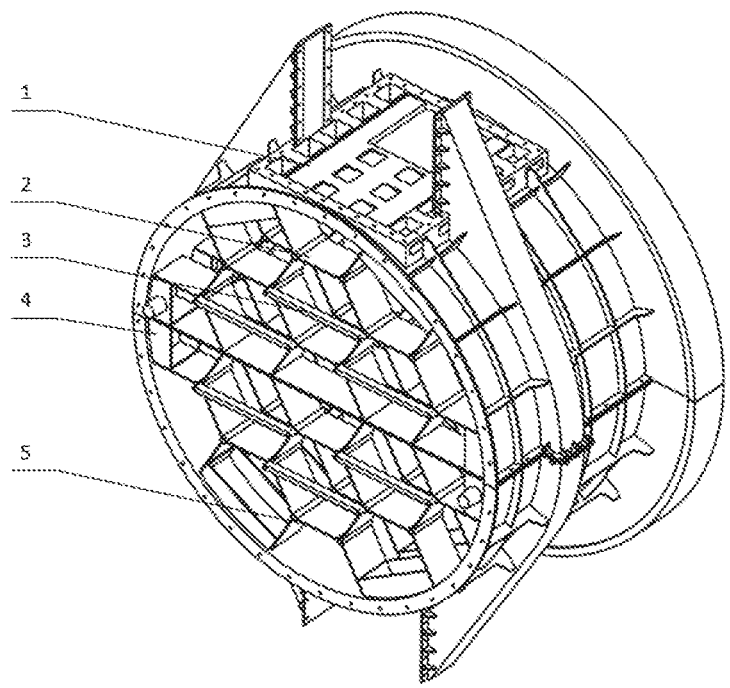
FIG. 1 is a perspective view of a honeycomb rib structure of the present disclosure.

Reference numerals: 1—cylindrical body, 2—upper honeycomb rib plate, 3—density increasing structure, 4—connecting structure, 5—lower honeycomb rib plate.

DETAILED DESCRIPTION OF EMBODIMENTS

The technical solutions of the present disclosure will be clearly and completely described below with reference to the embodiments. It is obvious that the described embodiments are only a part of the embodiments of the present disclosure. All other embodiments obtained by those skilled in the art based on the embodiments of the present disclosure without creative efforts fall in the scope of protection of the present disclosure.

Figure 3:
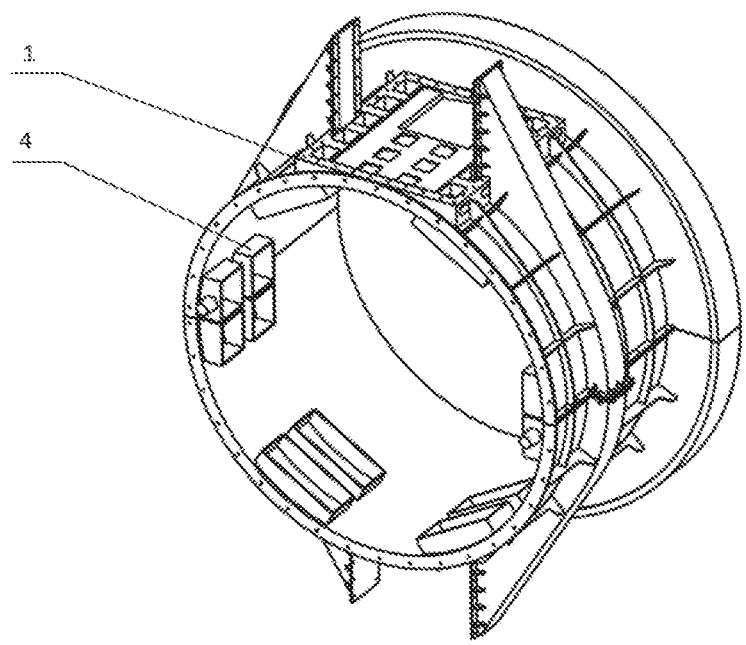
FIG. 3 is a perspective view of a cylindrical body of the honeycomb rib structure of the present disclosure.

As shown in FIG. 1, a honeycomb rib structure in a rotating gantry of a proton therapy device includes a cylindrical body 1, an upper honeycombed rib plate 2, a density increasing structure 3, a plurality of connecting structures 4 and a lower honeycombed rib plate 5. The cylindrical body 1 is the rotating gantry of the proton therapy device. As shown in FIG. 3, the upper and lower honeycombed rib plates are mounted in the cylindrical body 1.

Figure 2:
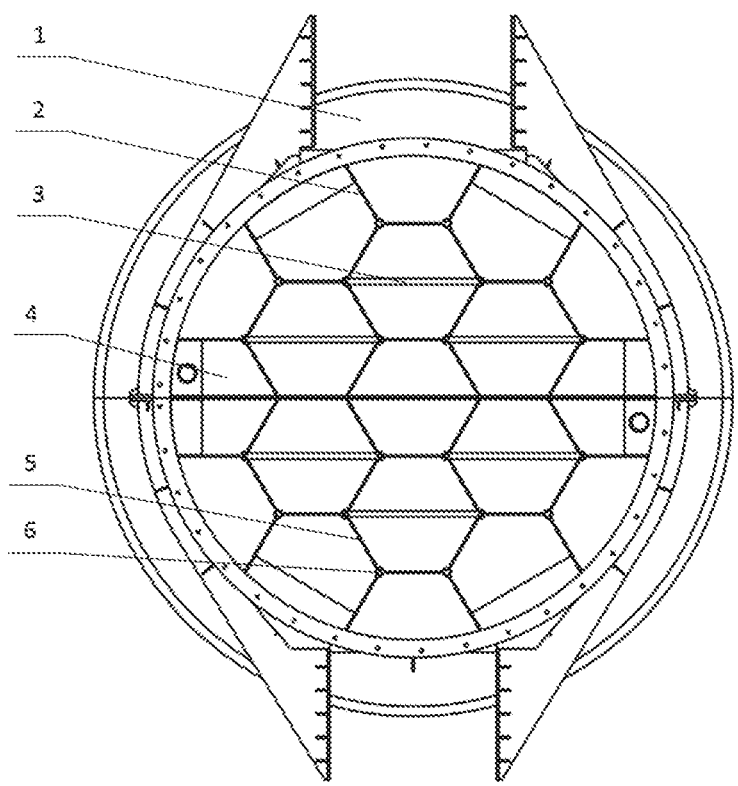
FIG. 2 is a schematic diagram of the honeycomb rib structure of the present disclosure, in which density increasing structures are added.
Figure 4:
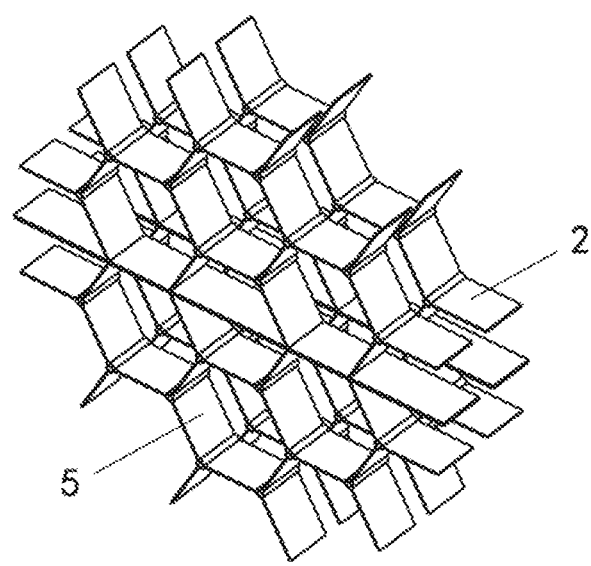
FIG. 4 is a perspective view of details of the honeycomb rib structure of the present disclosure.

As shown in FIGS. 1, 2 and 4, the upper honeycombed rib plate 2 and the lower honeycombed rib plate 5 are spliced by a plurality of basic structures, and each of the basic structures is in a regular hexagonal shape. Connecting nodes between the adjacent basic structures are ring structures 6. The ring structure 6 is in a columnar shape. A through hole is provided in the ring structure 6 in the radial direction, and the upper honeycombed rib plate 2 and the lower honeycombed rib plate 5 are connected through bolts.

The plurality of upper and lower honeycombed rib plates are connected to the cylindrical body 1 through the plurality of connecting structures 4. The plurality of connecting structures 4 provide welding points for the welding between the upper and lower honeycombed rib plates and the cylindrical body 1.

Specifically, as shown in FIG. 3, each of the plurality of connecting structures 4 has four casing walls in which every two casing walls with the same shape are oppositely arranged, respectively. The bottoms of the plurality of connecting structures 4 are fitted to the inner annular wall of the cylindrical body 1. The upper sides of the plurality of connecting structures 4 are open. Six pairs of the connecting structures 4 are uniformly arranged on the inner annular wall of the cylindrical body 1 in welded manner, and a plurality of clamping grooves are provided in the middle portions of two pairs of the plurality of connecting structures 4 which are correspondingly arranged. As shown in FIGS. 1-2, the plurality of connecting structures 4 are clamped by ring side openings of the upper and lower honeycombed rib plates, and straight plates of the upper and lower honeycombed rib plates are clamped in the plurality of clamping grooves in the middle portions of the corresponding connecting structures 4.

Figure 5:
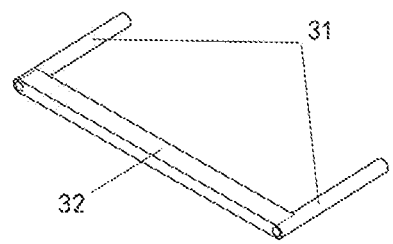
FIG. 5 is a perspective view of a density increasing structure of the honeycomb rib structure of the present disclosure.
Figure 6:
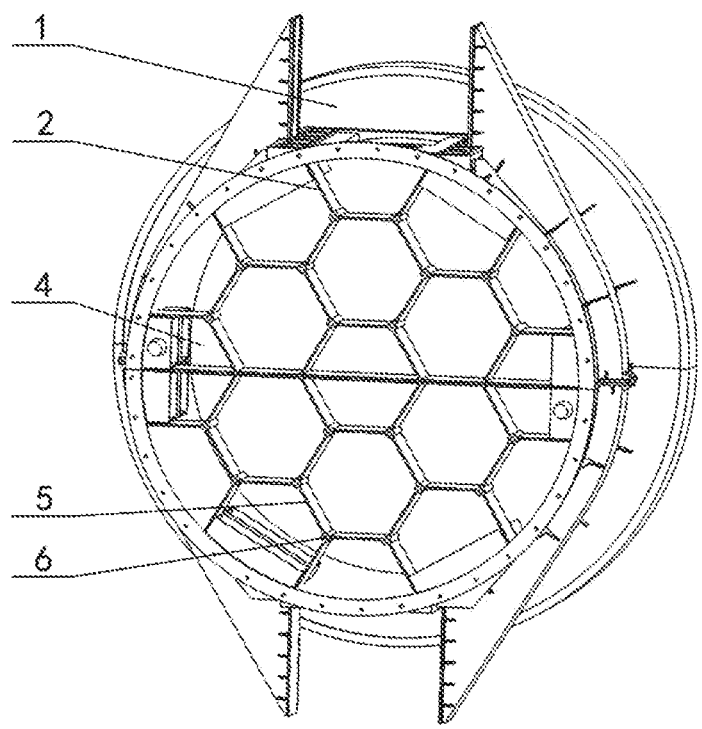
FIG. 6 is a schematic diagram of the honeycomb rib structure of the present disclosure, in which density increasing structures are removed.

The densities of the upper honeycombed rib plate 2 and the lower honeycombed rib plate 5 can be adjusted through the density increasing structure 3. The density increasing structure 3 is connected to the upper and lower honeycombed rib plates through the ring structure 6. Adding the density increasing structure 3 can increase the density of the upper and lower honeycombed rib plates to increase the structural strength. Specifically, as shown in FIG. 5, the density increasing structure 3 is in a U shape, and includes a connecting plate 32 and two round rods 31. Both end faces of the connecting plate 32 are perpendicularly connected to the two round rods 31, respectively. The connecting plate 32 is flush with connecting ends of the two round rods 31. The outer diameter of each of the two round rods 31 is matched with the inner diameter of the ring structure 6, and the two round rods 31 are inserted into the through hole of the ring structure 6.

The principles of the present disclosure are as follows:

The upper honeycombed rib plate 2 and the lower honeycombed rib plate 5 are of a honeycomb structure formed by a plurality of ribs and are arranged symmetrically. Each of the connecting nodes is of a ring structure to increase the connecting points. The density of the honeycombed rib plates can be adjusted as needed. The inner surface of the cylindrical body is connected to the outside of the honeycombed rib plates through the plurality of connecting structures.

The upper and lower honeycombed rib plates each are formed by a plurality of basic structures, and each of the basic structures is in a regular hexagonal shape. The upper and lower honeycombed rib plates are used to strengthen the internal structure of the rotating gantry which is the cylindrical body. The arrangement of the honeycomb ribs makes the space connecting to the inner surface of the cylindrical body fully satisfied. The connection nodes of the plurality of basic structures in a regular hexagonal shape which form the honeycomb rib structure are of the ring structure to increase the welding points, so that the structural strength is improved. The inner cavity of the ring structure can be configured to install the auxiliary support structure, and adjust the density of the honeycomb ribs. The outer edge of the honeycomb rib structure is connected to the inner surface of the cylindrical body through the designed enhancement structure to provide the welding positions for the honeycomb ribs, ensuring the structural strength.

INDUSTRIAL APPLICABILITY

The present disclosure realizes the lightweight of the rotating gantry under the premise of satisfying the structural strength of the rotating gantry of the proton therapy device, and the density of the honeycomb rib structure can be adjusted to satisfy requirements under the different working conditions due to the special structural design.

What is claimed is:

1. A honeycomb rib structure in a rotating gantry of a proton therapy device, comprising:
   an upper honeycombed rib plate, and a lower honeycombed rib plate, each honeycombed rib plate being formed into a substantially honeycombed shape defined by a plurality of hexagonal structures of substantially equal size;
   a plurality of connecting structures mounted on an inner annular surface of a cylindrical body of the rotating gantry;
   wherein the upper honeycombed rib plate and the lower honeycombed rib plate are symmetrically mounted to the plurality of connecting structures such that the upper honeycombed rib plate and the lower honeycombed rib plate substantially span a bore of the cylindrical body.

2. The honeycomb rib structure of claim 1, wherein
   the upper honeycombed rib plate and the lower honeycombed rib plate each have connecting nodes at a plurality of vertices of the plurality of hexagonal structures, each connecting node having a through hole;
   a plurality of density increasing structures, each having a connecting plate with a round rod connected to opposing end surfaces of the connecting plate;
   wherein the plurality of density increasing structures connect to the upper honeycombed rib plate or the honeycombed rib plate by inserting the round rods into the through holes of the connecting nodes.

3. The honeycomb rib structure of claim 2, wherein
   both connecting end surfaces of the connecting plate are perpendicularly connected to the two round rods, respectively, such that the density increasing structure forms a substantially U-shape;
   the connecting plate is flush with the connecting ends of the two round rods, such that the connecting plate is flush with either the upper honeycombed rib plate when the two round rods are inserted into the through holes; and
   an outer diameter of each of the two round rods is matched with an inner diameter of the through holes.

4. The honeycomb rib structure of claim 1, wherein the upper honeycombed rib plate and the lower honeycombed rib plate are connected through bolts.

5. The honeycomb rib structure of claim 1, wherein
   each of the plurality of connecting structures has four casing walls in which every two casing walls with the same shape are oppositely arranged, respectively;
   bottoms of the plurality of connecting structures are fitted to the inner annular wall of the cylindrical body;
   an upper side of each of the plurality of connecting structures is open;
   six pairs of the connecting structures are uniformly arranged on the inner annular wall of the cylindrical body in a welded manner; and
   a plurality of clamping grooves are provided in middle portions of two pairs of the six pairs of connecting structures which are correspondingly arranged.

6. The honeycomb rib structure of claim 5, wherein
   the plurality of connecting structures are clamped by ring side openings of the upper honeycombed rib plate and the lower honeycombed rib plate; and
   straight plates of the upper honeycombed rib plate and the lower honeycombed rib plate are clamped in the plurality of clamping grooves in the middle portions of the corresponding connecting structures.

* * * * *